United States Patent [19]

Davis

[11] Patent Number: 4,463,202
[45] Date of Patent: Jul. 31, 1984

[54] DI-ARYL MONOCHLOROPHOSPHINE WASTE TREATMENT

[75] Inventor: Gershon J. Davis, White Plains, N.Y.

[73] Assignee: Stauffer Chemical Company, Westport, Conn.

[21] Appl. No.: 408,980

[22] Filed: Aug. 17, 1982

[51] Int. Cl.³ .............................................. C07F 9/52
[52] U.S. Cl. ...................................... 568/16; 568/14; 568/17
[58] Field of Search .............................. 568/14, 16, 17

[56] References Cited

U.S. PATENT DOCUMENTS

| 3,105,097 | 9/1963 | Willans | 568/14 |
| 3,126,416 | 3/1964 | Willans | 568/14 |
| 3,459,808 | 8/1969 | Hall et al. | 568/14 X |
| 3,579,576 | 5/1971 | Angstadt | 568/14 X |

OTHER PUBLICATIONS

Buchner et al., JACS 73, pp. 755–756, (1951).
Kosolapoff, Organophosphorus Compounds, John Wiley & Sons, Inc., N.Y., pp. 43–46, 128 and 129, (1950).

Primary Examiner—Helen M. S. Sneed
Attorney, Agent, or Firm—Vivienne T. White

[57] ABSTRACT

A method of treating the residue generated in the production of diphenylphosphinous chloride is presented. The method comprises extracting the aluminum content of the residue by contacting the residue with an organic solvent to produce a mixture which when hydrolyzed results in a two-phase solution, the organic phase of which can be incinerated.

7 Claims, No Drawings

DI-ARYL MONOCHLOROPHOSPHINE WASTE TREATMENT

BACKGROUND OF THE INVENTION

1. Field of the Invention

The invention relates to the treatment of di-aryl monochlorophosphine waste residue and in particular to a method of treating the diphenylphosphinous chloride-aluminum chloride residue complexes derived from the manufacture of diphenylphosphinous chloride.

2. Related Art

Diphenylphosphinous chloride is a reaction derivative used as an intermediate for the production of U. V. stabilizers, polymerization catalysts and specialty products. A process for producing diphenylphosphinous chloride is by the Friedel-Crafts autogenous reaction of diphenyl dichlorophosphine in the presence of aluminum chloride. The reaction, in addition to producing phenyl dichlorophosphine, also produces a residue and phosphorus trichloride.

The residue obtained from this reaction is comprised of a complex having the formula $AlCl_3.2(C_6H_5)_2PCl$. The residue which reacts with water to produce HCl is liquid at 100° C. but is solid at ambient temperatures. The amount of residue generated in the process is dependent on the proportion of the catalyst used.

At the present time the residue is disposed of in drums in approved land-fill sites. Land-fill disposal of chemical waste has become increasingly controversial and alternative methods of safe waste disposal have been sought.

An object of the present invention is to develop an alternative means for disposing of waste material derived from the production of diphenylphosphinous chloride. A further object of the invention is to remove the aluminum metal from the residue so that the residue can safely be incinerated. Removal of the aluminum content of the residue is desirable to avoid damage to the refractory lining of the incinerator.

SUMMARY OF THE INVENTION

The invention is a novel method of treating wastes derived from the production of di-aryl monochlorophosphines and in particular diphenylphosphinous chloride (hereinafter DPC). The method comprises removing the aluminum metal so that the remaining residue can be incinerated. The disclosed process comprises of steps of:

(1) contacting the residue at a temperature at or above 100° C. with a solvent therefore form a homogenous mixture;

(2) hydrolyzing the mixture to produce a two-phase solution comprised of an organic phase and an aqueous phase;

(3) separating and recovering the organic phase from the aqueous phase.

The invention further comprises incinerating the recovered organic phase.

DETAILED DESCRIPTION OF THE INVENTION

A waste treatment method is disclosed for treating the waste derived from the production of di-aryl monochlorophosphines in general and specifically the diphenylphosphinous chloride-aluminum chloride residue derived from the production of DPC. The amount of residue derived from DPC production is dependent on the proportion of the catalyst utilized. The residue form is a complex having the formula $AlCl_3.2\phi_2PCl$.

The method of treating the waste as disclosed herein comprises removal of the aluminum metal and the incineration of the remaining residue. In the practice of the invention, the residue is mixed with an organic solvent which is water insoluble, which uniformly disperses (homogenize) the DPC residues and which is unreactive to $AlCl_3$. Suitable solvents are, for instance, benzene, chlorobenzene and the like. The term "homogenize" as used herein describes a mixture wherein the residue and solvent substantially dispersed throughout. The solvents primarily act to lower the viscosity of the residue.

In the practice of the invention chlorobenzene is the preferred solvent. The solvent is generally used in proportions of from about 20% to about 100% of the weight of the residue although there is no upper limit on the amount of solvent which can be used. The lowest practical proportions are generally from 20% to 50% of the solvent based on the weight of the residue since such amounts allow for easy separation of the organic and aqueous phases and are economical. Higher solvent use, although possible, would be uneconomical.

The solvent is added to the residue which is maintained at a temperature of from about 100° C. to 120° C. since below 100° C. the residue will solidify. The upper temperature limit is not critical but is primarily dependent upon the boiling point of the solvent utilized.

The contents of the solution, formed after contacting the residue with a suitable solvent, are hydrolyzed and a two-phase solution is formed, comprising a water phase and an organic phase. The following exemplifies the hydrolysis reaction

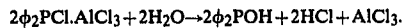

$$2\phi_2PCl.AlCl_3 + 2H_2O \rightarrow 2\phi_2POH + 2HCl + AlCl_3.$$

The amount of water added for the hydrolysis should be sufficient to keep all salts present in solution. A 4:1 water to residue mixture ratio is generally acceptable. The temperature for conducting the hydrolysis reaction is not critical. The hydrolysis can be conducted at room temperature but is preferably conducted at a temperature of from about 40° C. to about 50° C.

The aluminum chloride and HCl, after hydrolysis, are dissolved in the aqueous phase and can be further processed by known means such as neutralization, evaporation and periodic solid removal. The organic phase, containing the diphenylphosphine oxide waste ($2\phi_2POH$), can be incinerated. The following is presented as an example of the process of the invention.

EXAMPLE 1

To a 3-neck flask containing 445.1 grams of water was added 214.7 grams of a solution comprised of 154.6 grams of residue from the production of diphenylphosphinous chloride and 60.1 grams of chlorobenzene solvent, corresponding to 72% of residue to 28% chlorobenzene. The solution was added to the heated and stirred flask over a period of about 1 hour and simultaneously hydrolyzed. The temperature over the hydrolysis period ranged from a starting temperature of 23° C. to 48° C. The hydrolyzed solution was allowed to settle for about 1 hour after which time a two-phase solution resulted, comprising an aqueous phase and an organic phase. The starting residue, as obtained, contained approximately 8 grams of aluminum. Analysis of both phases after hydrolysis gave the following results for aluminum content:

| Method of Analysis | Phase | Wt. Amts./ Grams | Al Content | wt./gm. |
| --- | --- | --- | --- | --- |
| X-ray Florescence | Aqueous | 476.5 | 1.5% Al | 7 |
| Wet Chemistry | Organic | 175.5 | 0.4% Al | 1 |

What is claimed:

1. A method of treating the residue derived from the manufacture of di-aryl monochlorophosphine comprising:
    (a) contacting the residue with a solvent at a temperature above 100° C. to form a homogenous mixture;
    (b) hydrolyzing the contents of the solution to produce a two-phase mixture comprised of an organic phase and an aqueous phase;
    (c) separating and recovering the organic phase.

2. The method of claim 1 further comprising incinerating the recovered organic phase.

3. The method of claim 1 wherein the solvent is water insoluble.

4. The method of claim 1 wherein the solvent is unreactive to $AlCl_3$.

5. The method of claim 1 wherein the residue is contacted with the solvent in amounts generally ranging from about 20% to about 100% of the weight of the residue.

6. The method of claim 5 wherein the residue is contacted with the solvent in amounts of from 20% to 50% of the weight of the residue.

7. The method of claim 1 wherein the solvent is chlorobenzene.

* * * * *